Figure 1:
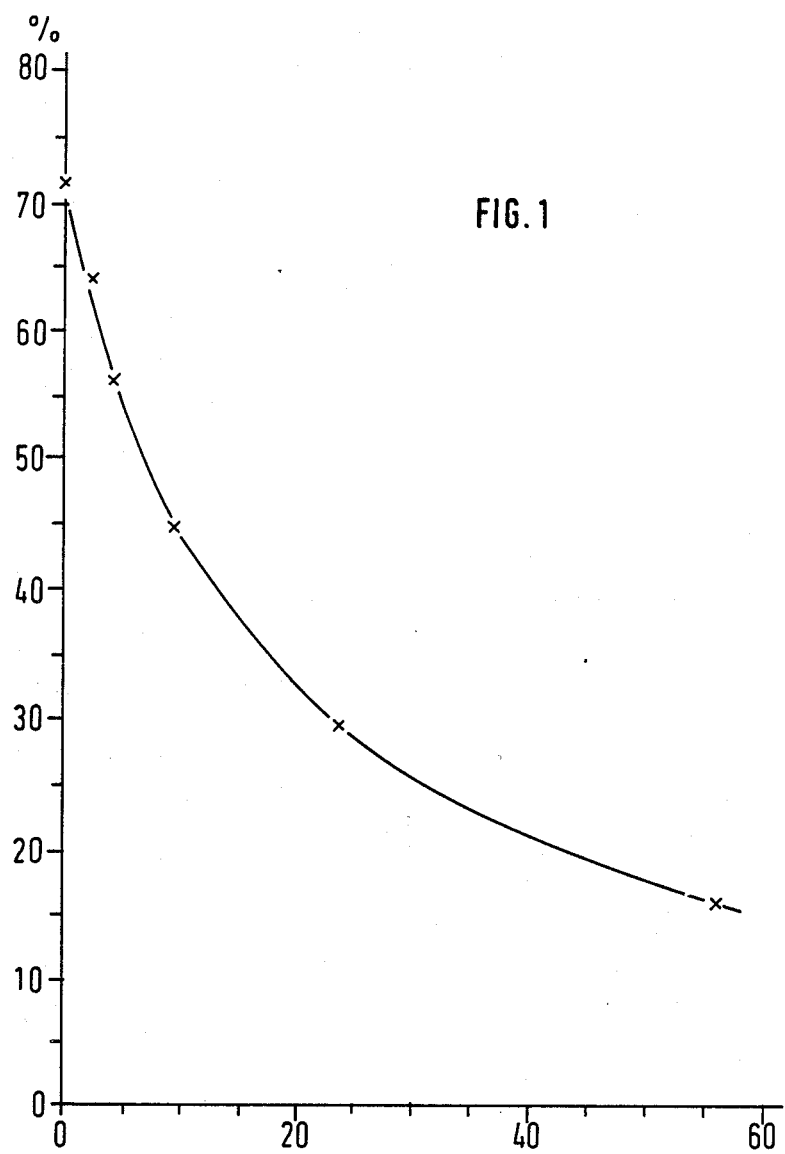

United States Patent [19]

Wissmann et al.

[11] Patent Number: 4,820,860
[45] Date of Patent: Apr. 11, 1989

[54] NOVEL THYRONINE DERIVATIVES

[75] Inventors: Hans Wissmann, Bad Soden am Taunus; Guido Simons, Ingelheim am Rhein; Helmut Strecker, deceased, late of Pfungstadt, all of Fed. Rep. of Germany, by Renate Strecker née Weihrauch, legal heir

[73] Assignee: Hoechst Aktiengesellschaft, Frankfurt am Main, Fed. Rep. of Germany

[21] Appl. No.: 087,805

[22] Filed: Aug. 21, 1987

[30] Foreign Application Priority Data

Aug. 25, 1986 [DE] Fed. Rep. of Germany ....... 3628795

[51] Int. Cl.$^4$ .................................... C07C 101/32
[52] U.S. Cl. ........................... 560/40; 560/27; 562/447; 436/500
[58] Field of Search ............... 560/40, 27; 562/447; 436/500

[56] References Cited

U.S. PATENT DOCUMENTS

| | | | |
|---|---|---|---|
| 3,410,891 | 11/1968 | Hughes et al. | 562/447 |
| 3,930,017 | 12/1975 | Kummer et al. | 560/40 |
| 4,358,604 | 11/1982 | Albarella et al. | 560/40 |
| 4,399,121 | 8/1983 | Albarella et al. | 560/40 |
| 4,608,389 | 8/1986 | Kisida et al. | 514/539 |
| 4,741,897 | 5/1988 | Andrews et al. | 560/40 |

FOREIGN PATENT DOCUMENTS 0052094 5/1982 European Pat. Off. .
0066989 12/1982 European Pat. Off. .

Primary Examiner—Paul Lieberman
Assistant Examiner—Helene Kirschner
Attorney, Agent, or Firm—Finnegan, Henderson, Farabow, Garrett & Dunner

[57] ABSTRACT

The invention relates to novel thyronine derivatives of the formula

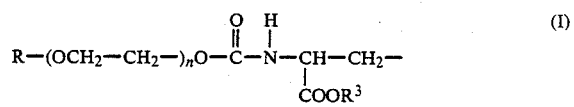

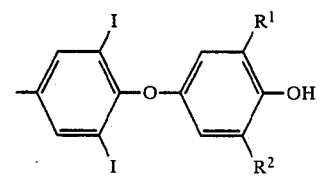

in which n is 10–400, R denotes H, alkyl or N-carbonyl-thyronine, $R^1$ and $R^2$ are identical or different and denote hydrogen or iodine, and $R^3$ denotes H or alkyl, a process for the preparation of the compounds, and their use when carrying out immunoassays.

8 Claims, 3 Drawing Sheets

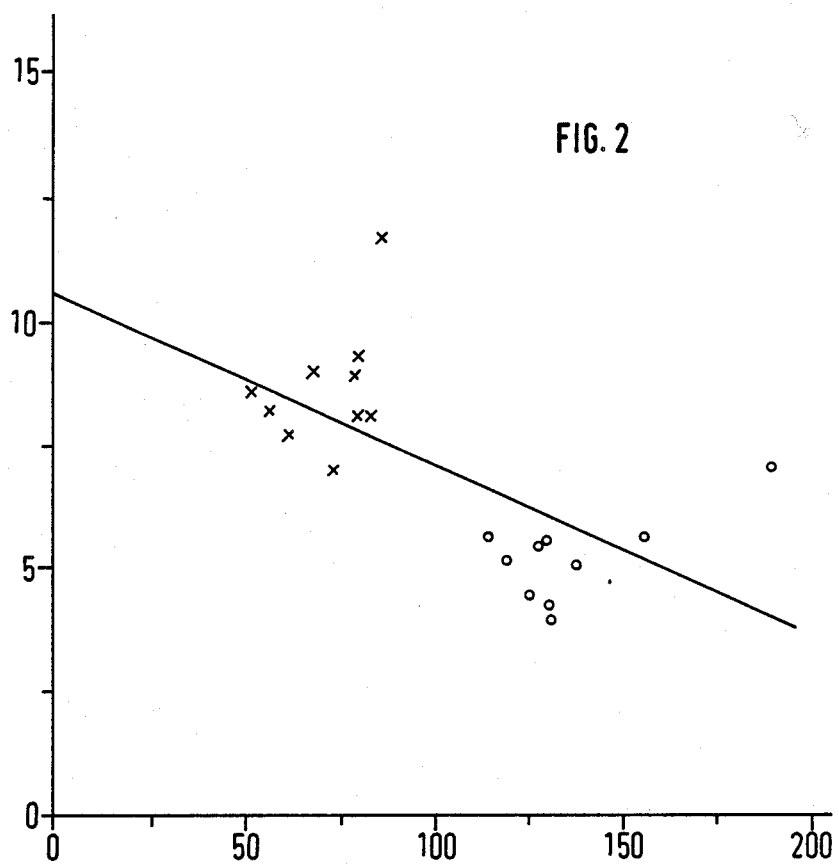

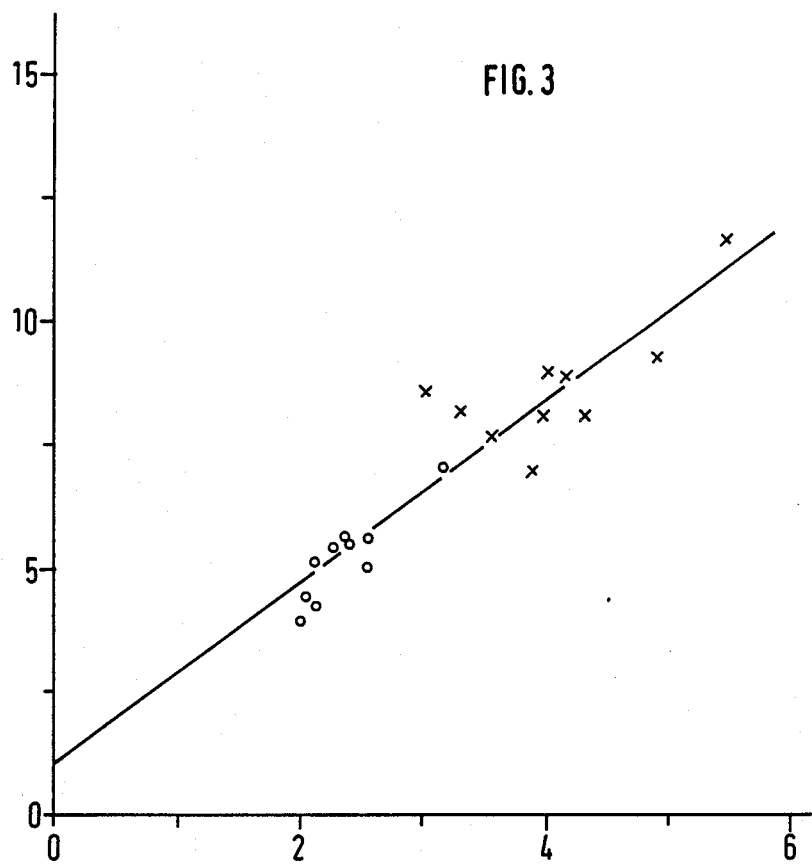

NOVEL THYRONINE DERIVATIVES

DESCRIPTION

The invention relates to novel tyronine derivatives of the general formula I

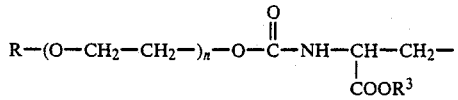

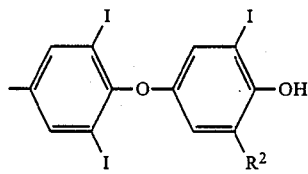

in which

R denotes hydrogen, $(C_1-C_6)$-alkyl or a group which can be quantified using chemical or physical methods, such as, for example, a radical of the formula

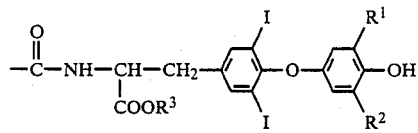

$R^1$ and $R^2$ are identical or different and denote iodine or hydrogen, $R^3$ denotes hydrogen or $(C_1-C_6)$-alkyl, and n represents an integer between 10 and 400, and the physiologically acceptable salts thereof with cations.

Preferred compounds of the formula I are those in which $R^1$ and $R^2$ are as defined above and n is 10-140, in particular 35-70, R denotes $(C_1-C_4)$-alkyl, in particular methyl or hydrogen, and $R^3$ denotes hydrogen or $(C_1-C_4)$-alkyl, in particular methyl or ethyl.

Salts of the compounds of the formula I are taken to mean, in particular, alkali metal, akaline-earth metal and ammonium salts.

A group which can be quantified using chemical or physical methods is taken to mean an organic radical which is used for labeling in an immunoassay. Such a radical can be labeled fluorescently, luminescently, electroactively, by spin or radioactively (cf. Neumüller, Römpps Chemie Lexikon [Römpps Lexicon of Chemistry], 8th Edition, Stuttgart 1983; Gunzer, Rieke, Kontakte Merck 1980, No.3, 3-11; Eckert, Angew. Chem. 88 [1976]565-574).

The invention furthermore relates to a process for the preparation of compounds of the formula I, wherein, in the compounds of the general formula II $$R\text{---}(O\text{---}CH_2\text{---}CH_2\text{---})_n\text{---}OH \quad (II)$$

in which R and n are as defined above, the free alcoholic OH group is reacted, either as carbonic acid ester chloride or as esters of carbonic acid substituted by suitable activated ester groups, with a compound of the formula III

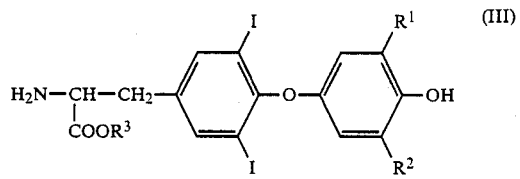

in which $R^1$ and $R^2$ are as defined above and $R^3$ denotes hydrogen, or, if appropriate, an ester of the formula III ($R^3\neq H$) is employed, the resultant esters of the formula I ($R^3\neq H$) are converted, if appropriate, into free acids of the formula I ($R^3=H$), and, if appropriate, the compound of the formula I thus obtained is converted into its salts.

The abovementioned compounds of the formula II are preferably treated with phosgene in inert anhydrous solvents (for example chlorinated hydrocarbons), analogously to the method described by W. Krey in Houben-Weyl, Mehoden der Organischen Chemie [Methods of Organic Chemistry](Georg Thieme Verlag, Stuttgart, 1952, Volume 8/III, p. 103) for the reaction of low-molecular-weight compounds. The carbonyl chloride derivatives thus produced are then reacted with the di-, tri- or tetraiodothyronine derivatives of the general formula III described.

Instead of the chlorides, other activated derivates of carbonic acid, for example the N-hydroxy-succinimide esters, pentachlorophenyl esters, nitrophenyl esters and the like can also be used.

The reaction of the abovementioned carbonic acid derivatives with compounds of the formula III is carried out in a mixed aqueous medium at a pH of 7-10, preferably 8.5-10. The solvents used are dimethylformamide/water, or dimethylacetamide/water. Unreacted thyronine derivative of the formula III is removed by dialysis, ®Sephadex chromatography or ultrafiltration, for example through a UM 2 membrane (Messrs. Amicon).

Due to the preparation procedure, mixtures of two or more compounds for the formula I are generally produced. The invention therefore also relates to preparation which contain two or more compounds of the formula I.

The invention furthermore relates to the use of compounds of the formula I or mixtures thereof when carrying out an immunoassay, preferably a radioimmunoassay.

The following examples serve to illustrate the present invention without it being limited to these.

Example 1

(Polyethylene glycol)-bis-oxycarbonyl-L-3,3',5-triiodothyronine 220 mg (0.3 mmol) of L-triiodothyronine are dissolved with stirring in a mixture of 4 ml of dimethylformamide and 4 ml of water with addition of aqueous 2N NaOH in an autotitrator at pH 10. DMF and subsequently, in portions, within 1 hour, 1 g of (polyethylene glycol)-bis-oxycarbonyl chloride of molecular weight 6000 are then added. The mixture is allowed to react for a further 12 hours at room temperature and pH 9.5, a small amount of insoluble material is filtered off, the solution is evaporated to dryness in high vacuum at room temperature, the residue is taken up in 100 ml of water, and the solution is acidified to pH 3 using aqueous 1N HCL. The solution thus obtained is dialyzed against a total of 30 liters of water, and the final product is isolated by freeze drying. The pale yellowish solid thus obtained exhibits an iodine content of 11%, which corresponds to a content of bound triiodothyronine of about 1.7 mol/mol of thyronine derivative.

Yield: 975 mg

Example 2

Monomethyl-(polyethylene glycolyl)oxycarbonyl-L-3.5-diiodothryonine compound 940 mg (2 mmol) of L-diiodothyronine are dissolved in a mixture of 6 ml of dimethylformamide and 3 ml of water at pH 8.8-9.5 in an autotritator. 1 g of monomethyl(polyethylene glycol)oxycarbonyl chloride (molecular weight 750) is then added in portions within 1 hour. After stirring for a further 30 minutes at room temperature, a further 1 g of the carbonyl chloride described above is added. After stirring over night, the solution is virtually clear. The solvent is evaporated in a high vacuum at room temperature, and the residue is taken up in 30 ml of water, the solution is acidified to pH 3 using dilute hydrochloric acid, the water phase is extracted repeatedly with methylene chloride, the methylene chloride phase is dried over magnesium sulfate, and a colorless oil, which, according to elemental analysis (C, H, I), contains about 30% of the monomethyl-(polyethylene glycol)-diiodothyronine compound, is obtained after removing the methylene chloride by distillation.

Yield: 2.5 g

Further purification is effected by column chromatography on (R)Sephade×G 10 in aqueous 0.1 M acetic acid.

Yield: 0.5 g of a preparation which is 80% strength according to elemental analysis.

Example 3

Monomethyl-(polyethylene glycolyl)oxycarbonyl-L-3,3', 5,5'-tetraiodothyronine compound 350 mg of L-3,3', 5,5'-tetraiodothyronine are dissolved in a mixture of 4 ml of dimethylformamide and 4 ml of water through addition of aqueous 0.5 N sodium hydroxide solution at pH 9.5. A solution of 1 g of (polyethylene glycol)-methyl ether carbonyl chloride (molecular weight about 1900) in 4 ml of dimethylformamide is added dropwise to this solution within 1 hour with stirring and maintenance of the pH at 9.5. During the addition of the acid chloride, the suspension produced initially redissolves. After allowing to stand overnight, the solution is acidified to pH 3 using dilute hydrochloric acid, and the solvent is removed by distillation in a high vacuum at room temperature. The residue is dried in a desiccator, and is subsequently washed by boiling three times with absolute ether. The residue is then taken up in 16 ml of boiling methyl chloride, separated from undissolved material by filtration and then allowed to cool in an ice bath.

The precipitated solid is filtered off under suction: 565 mg. By concentrating the mother liquor, a further fraction is obtained: 200 mg. The two fractions exhibit development distances in the chloroform/methanol/20% strength formic acid (69:30:7.5) TLC system which are identical to one another and different from 3,3',5,5'-tetraiodothyronine and exhibit identical elemental analyses, which indicate about 1 mol of bound 3,3',5,5'-tetraiodothyronine/mol of the compound.

Example 4

(Polyethylene glycolyl)oxycarbonyl-diiodothyronine compound 470 mg of 3,3-diiodothyronine and a 2.2 g of (polyethylene glycol)-bis-oxycarbonyl chloride (molecular weight 6000) are reacted as described under Example 2, but worked up after a reaction time of only 1 hour. 2.8 g of a colorless solid which has a waxy consistency and which contains, according to the elemental analysis (iodine, C, H), about 80% of the polymer substituted by 1 mol of 3,3-diiodothyronine, are obtained. Thin-layer chromatography, as described in Example 3, shows the difference between the reaction product and the starting material.

Example 5

Monomethyl-(polyethylene glycolyl)oxycarbonyl-L-3,5diiodothyronine compound

The compound is prepared as described in Example 2, but using the carbonyl chloride of a monomethyl-(polyethylene glycol) of molecular weight 3000. According to the elemental analysis, the crude product comprises 50% of the title compound.

Yield: 3.1 g of a colorless, semi-solid substance.

Example 6

(Polyethylene glycol)oxycarbonyl-L-3,3',5-triiodothyronine methyl ester

The compound was prepared as described by the Example 1, but using L-triiodothyronine methyl ester in place of L-triiodothyronine and using a (polyethylene glycol)-bisoxycarbonyl chloride of molecular weight 15,000. The reaction time was shortened to 2 hours. According to the elemental analysis, the reaction product produced showed incorporation of 1 mol of L-triiodothyronine methyl ester/mol of polyethylene glycol.

Yield at the same batch by weight as in Example 1: 750 mg.

Example 7

Procedure for determining FT4 by the 2-step method (in this respect, cf. Eckert, Angew, Chem. 88 [1976]565-574).

In tubes coated with T4 antibodies (20 ng of antibody/tube), 200 μl of a standard series (human serums with increasing FT4 content) and 1000 μl of buffer are brought into contact for half an hour with shaking.

After pouring out the reaction solution, 1000 μl of the tracer prepared from the compound of Example 3 (activity about 60,000 impulses per minute) are poured into the pre-incubated tube. The tube is incubated for 1 hour, and the unbound tracers are separated off and measured in a γ-counter.

FIG. 1 shows the standard curve of human serums with increasing FT4 content. The tracer was prepared from the derivative described in Example 3.

FIGS. 2 and 3 show results from the investigation of human serums (shown as "x"). The serums of pregnant women (shown as "o") were included in the investigation since they have a high total T4 content. The two correlations show that there is no direct relationship between the content of free T4 and the total T4 content. The correlations furthermore show that the T4/TBG

We claim:
1. A compound of the formula I

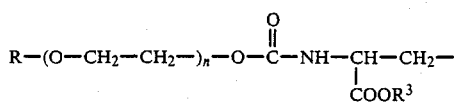

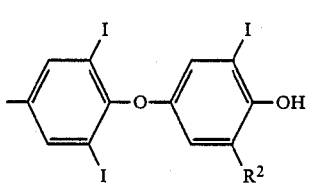

in which
R denotes hydrogen, (C$_1$-C$_6$)-alkyl or a radical of the formula

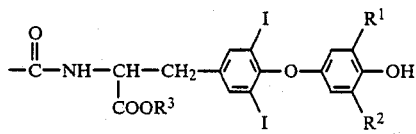

R$^1$ and R$^2$ are identical or different and denote iodine or hydrogen,
R$^3$ denotes hydrogen or (C$_1$-C$_6$)-alkyl, and
n represents an integer between 10 and 400,
and the physiologically acceptable salts thereof with cations.

2. A compound of the formula I as claimed in claim 1, in which n is 35-70, R denotes H or (C$_1$-C$_4$)-alkyl, and R$^3$ denotes hydrogen or (C$_1$-C$_4$)-alkyl.

3. A compound of the formula I as claimed in claim 1, in which R$^3$ denotes hydrogen, methyl or ethyl.

4. A compound of the formula I as claimed in claim 1, in which at least one of the iodine atoms is radioactively labeled.

5. A compound of the formula I, in which R$^1$, R$^2$, R$^3$ and n are as defined in claim 1 and R is a radical of the formula

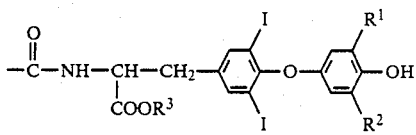

and the physiologically acceptable salts thereof with cations.

6. A method of carrying out an immunoassay which comprises using in said immunoassay an effective amount of a compound of the formula I as claimed in claim 1.

7. A composition containing a mixture of two or more compounds of the formula I as claimed in claim 1.

8. A method of carrying out an immunoassay which comprises using in said immunoassay an effective amount of a composition as claimed in claim 7.

* * * * *

UNITED STATES PATENT AND TRADEMARK OFFICE
CERTIFICATE OF CORRECTION

PATENT NO. : 4,820,860
DATED : April 11, 1989
INVENTOR(S) : Hans Wissmann et al.

It is certified that error appears in the above-identified patent and that said Letters Patent is hereby corrected as shown below:

Claim 4, column 6, lines 9-10: "radioactivately" should be --radioactively--.

Signed and Sealed this

Fifteenth Day of May, 1990

Attest:

HARRY F. MANBECK, JR.

*Attesting Officer*  *Commissioner of Patents and Trademarks*